(12) United States Patent
Kohashi et al.

(10) Patent No.: US 6,567,692 B1
(45) Date of Patent: May 20, 2003

(54) BODY FAT MEASURING INSTRUMENT

(75) Inventors: Toru Kohashi, Hyogo (JP); Kenji Mitao, Kakogawa (JP)

(73) Assignee: Yamato Scale Co., Ltd., Hyogo (JP)

( * ) Notice: Subject to any disclaimer, the term of this patent is extended or adjusted under 35 U.S.C. 154(b) by 89 days.

(21) Appl. No.: 09/850,743

(22) PCT Filed: Sep. 29, 2000

(86) PCT No.: PCT/JP00/06816
§ 371 (c)(1),
(2), (4) Date: May 18, 2001

(87) PCT Pub. No.: WO01/24694
PCT Pub. Date: Apr. 12, 2001

(30) Foreign Application Priority Data

Oct. 7, 1999 (JP) .................... 11-286156

(51) Int. Cl.[7] ................... A61B 5/05
(52) U.S. Cl. ..................... 600/547
(58) Field of Search .............. 600/547, 372, 600/548, 384, 386, 393

(56) References Cited

U.S. PATENT DOCUMENTS

| | | | |
|---|---|---|---|
| 5,579,782 A | | 12/1996 | Masuo |
| 5,720,296 A | * | 2/1998 | Cha .................... 600/554 |
| 6,370,425 B1 | * | 4/2002 | Oguma .................... 600/547 |
| 6,393,317 B1 | * | 5/2002 | Fukuda et al. .............. 600/547 |
| 6,400,983 B1 | * | 6/2002 | Cha .......................... 600/547 |

FOREIGN PATENT DOCUMENTS

| | | |
|---|---|---|
| JP | 7-51242 | 2/1995 |
| JP | 7-79938 | 3/1995 |
| JP | 9-51883 | * 2/1997 |
| JP | 10-510455 | 10/1998 |
| JP | 11-113872 | 4/1999 |
| JP | 2001-170019 | * 6/2001 |
| WO | WO99/20175 | 4/1999 |

* cited by examiner

*Primary Examiner*—John A. Jeffery
(74) *Attorney, Agent, or Firm*—Armstrong, Westerman & Hattori, LLP.

(57) ABSTRACT

With a very simple arrangement, body composition impedance, which excludes contact impedance between the dermal surface of a patient and each electrode and body distal site surrounding composition impedance, is measured thereby measuring the amount of body fat with high accuracy. Two pairs of electrodes (four electrodes in total) are connected to a constant current circuit through analog switches respectively. The electrodes to which a constant current is applied are sequentially switched by control signals output from an arithmetic operation control unit. By use of output voltage signals from an operational amplifier, a CPU in the arithmetic operation control unit calculates the value of the body composition impedance by removing the contact impedance and the body distal site surrounding composition impedance.

11 Claims, 11 Drawing Sheets

BODY FAT MEASURING INSTRUMENT

TECHNICAL FIELD

The present invention relates to a body fat measuring device for measuring the amount of fat in a human body.

BACKGROUND ART

The body composition of a human body is made up of muscles, bones, fat and others. The value of impedance of a human body containing a large amount of fat components differs from that of a human body containing a large amount of muscle components. More specifically, bio-impedance has such a nature that as fat components increase, the value of impedance increases and as components containing water increase, the value of impedance drops. When obtaining the amount of fat contained in the body composition by utilizing this nature, the following method is usually taken: Electrodes are attached to dermal surfaces at distal sites of the body such as the tips of fingers of right and left hands, the tiptoes of right and left feet, and the soles of right and left feet. An alternate current or voltage having a frequency of about several tens of KHz to 100 KHz is applied to these electrodes to measure the impedance of the body composition present between the distal sites. Then, the amount of body fat is calculated from the value of impedance thus obtained and personal data such as age, sex and height.

In recent years, the amount of fat contained in the body composition has been considered to be an index for health care and attracted the attention of ordinary people a great deal. Accordingly, demands toward body fat measuring devices for family or personal use have been increasingly growing. With such a background, there have been developed and sold a variety of inexpensive body fat measuring devices capable of measuring the amount of body fat with easy operation.

Known body fat measuring devices generally employ the measuring method called "the two terminal method" (the two electrode method) or the measuring method called "the four terminal method" (the four electrode method), and measure the amount of body fat in the body composition by measuring, in an easy way, body inter-distal-site impedance (i.e., the impedance between discrete distal sites of the body to which electrodes are attached) or body composition impedance that excludes the composition of the body at the distal sites.

FIG. 9(a) is a measurement principle diagram illustrating the principal of measurement of body composition impedance by a body fat measuring device which utilizes the conventional two terminal method and FIG. 9(b) is a circuit diagram for explaining the measurement principle. This body fat measuring device 100 comprises two electrodes 101a, 101b on its top surface. The two electrodes 101a, 101b are connected to a constant current circuit 102 and a patient steps on the measuring device 100 with one foot placed on the electrode 101a and the other foot on the electrode 101b, so that a constant current Ic is supplied to the human subject from the constant current circuit 102. The constant current circuit 102 is comprised of (i) an operational amplifier 103 for outputting the constant current Ic and (ii) a reference resistor 104 having a given value Rs for controlling the circuit so as to allow the operational amplifier 103 to output the constant current Ic. The electrodes 101a, 101b are connected to a voltage measurement circuit 105 and a voltage V generated between the electrodes 101a, 101b in a condition in which the constant current Ic is applied thereto is measured by the voltage measurement circuit 105. The voltage measurement circuit 105 comprises (i) an operational amplifier 106 for outputting the voltage V generated between the electrodes 101a, 101b in response to a voltage signal released from the electrodes 101a, 101b; (ii) input resistors 107a, 107b for the operational amplifier 106; and (iii) a resistor 108 for a negative feedback circuit.

In the thus-arranged body fat measuring device 100, where the body inter-distal-site impedance is Zo, the contact impedance between the electrode 101a and the dermal surface of a foot of the human subject is RX1, the contact impedance between the electrode 101b and the dermal surface of another foot is RY1, the relationship represented by the following equation exists between the impedances Zo, RX1, RY1, the constant current Ic, and the voltage V.

$$(RX1+Zo+RY1) \cdot Ic = V$$

That is, $$Zo+RX1+RY2 = V/Ic$$

Herein, if the sum of the contact impedances RX1, RY1 (RX1+RY1) is much smaller than the body inter-distal-site impedance Zo, in other words, if Zo+RX1+RY2≈Zo, the body inter-distal-site impedance Zo can be obtained.

By performing calculation based on the body inter-distal-site impedance Zo thus obtained and personal data such as the age, sex and height of the patient which have been input to the body fat measuring device 100 beforehand, the amount of body fat can be obtained. It should be noted that the body inter-distal-site impedance Zo is obtained by combining body distal site surrounding composition impedance to body composition impedance.

Next, a body fat measuring device using the conventional four terminal method will be explained. FIG. 10(a) is a diagram showing the measurement principal of a body composition impedance in a body fat measuring device which utilizes the conventional four terminal method and FIG. 10(a) is a circuit diagram for explaining the measurement principle. The body fat measuring device 110 comprises four electrodes 111a, 111b, 112a and 112b on the top surface thereof. A patient steps on the measuring device 110 with one foot placed on the electrodes 111a, 112a and the other foot on the electrodes 111b, 112b. The electrodes 111a, 111b are connected to a constant current circuit 113, and when the patient puts one foot on the electrode 111a and the other on the electrode 111b, a current Id is supplied to the human subject from the constant current circuit 113.

The electrodes 112a, 112b are connected to a voltage measurement circuit 114 and a voltage generated between the electrodes 112a, 112b when the constant current Id is applied thereto is measured. Herein, the constant current circuit 113 is comprised of (i) an operational amplifier 115 for outputting the constant current Id and (ii) a reference resistor 116 having a given value Rs for controlling the circuit so as to allow the operational amplifier 115 to output the constant current Id. The voltage measurement circuit 114 is comprised of (i) an operational amplifier 117 for outputting the voltage V generated between the electrodes 112a, 112b in response to a voltage signal released from the electrodes 112a, 112b; (ii) input resistors 118a, 118b for the operational amplifier 117; and (iii) a resistor 119 for a negative feedback circuit.

In the thus-arranged body fat measuring device 110, where the body composition impedance to be measured is Zi, the contact impedances between the electrodes 111a, 111b, 112a, 112b and the dermal surfaces of the feet of the human subject are RX1, RY1, RX2 and RY2, respectively, the resistance values of the input resistors 118, 118b of the operational amplifier 117 are set to be sufficiently higher than the contact impedances RX2, RY2, whereby the constant current Id to be supplied between the electrodes 111a, 111b will not flow into the operational amplifier 117 and the amplification factor of the operational amplifier 117 will not be affected even if the contact impedances RX2, RY2 fluctuate. Accordingly, a voltage generated between virtual intersections P and Q in the body, that is, the voltage V generated at both ends of the body composition impedance Zi excluding the contact impedances and body distal site surrounding composition impedances can be measured by the voltage measurement circuit 114. Zi is calculated from the equation Zi=V/Id based on the voltage V thus obtained and the constant current value Id, thereby obtaining the body composition impedance Zi that is not affected by the contact impedances and the body distal site surrounding composition impedances. Regarding the body distal site surrounding composition impedances, since articulates have great impedance values irrespective of the amount of body fat, it is necessary to measure impedance which excludes the impedances of the compositions surrounding body's distal sites particularly in cases where the composition to be measured includes articulates.

The amount of fat in the body of the patient can be obtained by calculation based on the body composition impedance Zi thus obtained and personal data such as the age, sex, height etc. of the patient which have been input to the body fat measuring device 110 beforehand.

As prior art techniques associated with the present invention, there are proposed body fat measuring devices in Japanese Patent Publication (KOKAI) Gazette No. 7-79938 (1995) and Published Japanese Translations of PCT International Publication for Patent Applications No. 10-510455 (1998), according to which the impedance of an internal organ in a body is measured by the above-described four terminal method to be utilized in measuring the amount of fat. FIG. 11 diagrammatically shows the principle of the measurement of an internal organ composition impedance Zj in the above prior art body fat measuring devices.

In a body fat measuring device 120 associated with the above prior art, there are provided eight electrodes $E_1$, $E_2$, $E_3$, $E_4$, $E_5$, $E_6$, $E_7$, and $E_8$ which are paired and attached to the right-left pairs of sites on the hands and foot of a human subject, respectively. One group of the electrodes $E_1$, $E_3$, $E_5$, $E_7$ is connected to a constant current circuit, whereas the other group of the electrodes $E_2$, $E_4$, $E_6$, $E_8$ is connected to a voltage measurement circuit. It should be noted that these constant current circuit and voltage measurement circuit have the same configuration as those of the above-described body fat measuring devices 100, 110 which utilize the two terminal method and the four terminal method, respectively. In the thus-arranged body fat measuring device 120, a current is applied between the electrodes $E_1$ and $E_3$ and the voltage between the electrodes $E_2$ and $E_4$ is measured, thereby obtaining the value of ① $Z_1+Z_2$. Similarly, a current is applied between the electrodes $E_5$ and $E_7$ and the voltage between the electrodes $E_6$ and $E_8$ is measured, thereby to obtain the value of ② $Z_4+Z_5$; a current is applied between the electrodes $E_1$ and $E_5$ and the voltage between the electrodes $E_2$ and $E_6$ is measured, thereby obtaining the value of ③ $Z_1+Zj+Z_4$; and a current is applied between the electrodes $E_3$ and $E_7$ and the voltage between the electrodes $E_4$ and $E_8$ is measured, thereby obtaining the value of ④ $Z_2+Zj+Z_5$. Based on the results of these measurements, the internal organ composition impedance Zj is calculated from the equation {③+④−(①+②)}/2. Then, the amount of body fat is calculated from the internal organ composition impedance Zj.

Japanese Patent Publication (KOKAI) Gazette No. 5-49050 (1993) discloses a body fat measuring device in which body inter-distal-site impedance which is composed of body composition impedance and body distal site surrounding composition impedance is measured, and the amount of body fat is calculated based on the measured impedance and the personal data on the patient.

Since the body fat measuring device 110 shown in FIG. 10 and utilizing the four terminal method is designed to measure a voltage generated in the body composition that excludes the composition surrounding body distal sites from the contact impedance between the feet of the human subject and from the all the impedances present between the distal sites of the body, the measuring device 110 requires the operational amplifier 117 which constitutes the voltage measurement circuit 113, the input resistors 118a, 118b for the operational amplifier 117, and the resistor 119 for the feedback circuit. As a result, the configuration of the measuring device becomes large in scale, and the number of wires and circuits increases, inevitably leading to increased cost.

The prior art body fat measuring device 110 utilizing the four terminal method needs a pair of electrodes (two electrodes) for each measuring point (four electrodes in total) in order to measure the body composition impedance Zi from two sites of the body. In addition, wires and various circuits are connected to each electrode so that a large system configuration is involved, resulting in increased cost.

The prior art body fat measuring device 100 shown in FIG. 9 and employing the two terminal method has another problem. This device 100 is designed to obtain the body inter-distal-site impedance Zo including the contact impedances RX1, RY1 upon condition that the sum of the contact impedances RX1, RY1 is sufficiently smaller than the body inter-distal-site impedance Zo. Since a different amount of water and other deposits are present on the dermal surface of a body in each occasion, the values of the contact impedances RX1, RY1 vary more or less so that it becomes difficult to correctly, stably obtain the body inter-distal-site impedance Zo. Additionally, the body inter-distal-site impedance Zo includes the impedance of the composition surrounding body distal sites and, therefore, the impedance Zo sometimes has a great impedance value irrespective of the amount of fat within the body of the patient. As a result, the body fat measuring device 100 fails in correctly measuring the amount of body fat.

The body fat measuring device 120 for measuring the internal organ composition impedance Zj shown in FIG. 11 also suffers from problems: Since it needs eight electrodes in total (two electrodes for each hand and each foot), many wires and circuits become necessary which leads to a large system configuration and increased cost. In addition, when measuring the impedance of the cross section of the trunk of a body, many pairs of electrodes are attached with the trunk between each pair, and a voltage is measured between each opposed pair of electrodes. In this case, a pair of electrodes is necessary for each measuring point so that a large number of electrodes are involved, resulting in increases in the number of wires and circuits and in cost.

The body fat measuring device disclosed in Japanese Patent Publication (KOKOKU) Gazette No. 5-49050 measures the body inter-distal-site impedance that includes the body distal site surrounding composition impedance having a large value irrespective of the amount of body fat and obtains the amount of body fat based on the measured body inter-distal-site impedance. Therefore, this measuring device also has difficulty in correctly measuring the amount of body fat.

The present invention is directed to overcoming the above-described problems and a prime object of the invention is therefore to provide a body fat measuring device capable of accurately measuring body composition impedance which excludes contact impedance generated between each electrode and the dermal surface of a human object and body distal site composition impedance so that the amount of fat within the body of the human subject can be measured with high accuracy.

DISCLOSURE OF THE INVENTION

In accomplishing the above prime object, there has been provided, in accordance with the invention, a body fat measuring device for measuring the amount of body fat within a body, the device comprising:

(a) a single or a plurality of electrodes in contact with each of a plurality of sites on the dermal surface of the body;

(b) a power supply circuit for applying a constant current or voltage to the electrodes;

(c) impedance measuring means for switching the electrodes to be connected to the power supply circuit such that a contact impedance and a body distal site surrounding composition impedance are present between the electrodes or such that a contact impedance, a body distal site surrounding composition impedance and a body composition impedance are present between the electrodes, whereby the value of the composite of the contact impedance and the body distal site surrounding composition impedance and the value of the composite of the contact impedance, the body distal site surrounding composition impedance and the body composition impedance are respectively measured; and (d) calculating means for calculating the value of the body composition impedance based on the measured values obtained by the impedance measuring means.

In the invention, one or a plurality of electrodes are disposed so as to contact each of a plurality of sites on the dermal surface of a body. The impedance measuring means measures the value of the composite of a contact impedance and a body distal site surrounding composition impedance and the value of the composite of a contact impedance, a body distal site surrounding composition impedance, and a body composition impedance. The calculating means then calculates only the value of the body composition impedance, based on the measured values. Personal data (age, sex, height, etc.) on a patient have been input beforehand, and the amount of body fat (body fat percentage) is calculated from the calculated value of the body composition impedance and the personal data, using a known method.

According to the invention, since the impedance measurement is made with different combinations of electrodes to which a current or voltage is applied, the influences of the contact impedances and the body distal site surrounding composition impedances are thoroughly eliminated by calculation so that a highly accurate body composition impedance value in which the amount of body fat of the patient is reflected and, consequently, a highly accurate body fat amount can be calculated. Since the need for electrodes for measuring a voltage generated within the body and a voltage measurement circuit can be obviated, the system construction can be simplified, leading to cost reduction.

The invention is preferably arranged as follows. The electrodes are provided such that a pair of electrodes are disposed so as to contact a first one of two dermal surface sites between which a body composition impedance to be measured is present and another pair of electrodes are disposed so as to contact a second one of the dermal surface sites. The electrodes in each pair are close to each other. The power supply circuit is connected to the pair of electrodes at the first site or at the second site by the impedance measuring means to measure the value of the composite of a contact impedance and a body distal site surrounding composition impedance, these impedances being present between the pair of electrodes to which the power supply circuit is connected. The power supply circuit is connected to one of the electrodes in the respective pairs at the first site and at the second site to measure the value of the composite of a contact impedance, a body distal site surrounding composition impedance and a body composition impedance, these impedances being present between the electrodes to which the power supply circuit is connected. The calculating means calculates the value of the body composition impedance based on the measured values.

With this arrangement, the influences of the contact impedances and the body distal site surrounding composition impedances can be thoroughly eliminated, similarly to the above case so that the value of the body composition impedance in which the amount of body fat of the patient is reflected can be calculated with high accuracy and the system configuration can be simplified, resulting in cost reduction.

The invention may be also arranged as follows. The electrodes are provided such that two electrodes are disposed so as to contact a first one of two dermal surface sites between which a body composition impedance to be measured is present and one electrode is disposed so as to contact a second one of the two sites. The two electrodes disposed at the first site are close to each other. The power supply circuit is connected to the two electrodes at the first site by the impedance measuring means to measure the value of the composite of a contact impedance and a body distal site surrounding composition impedance, these impedances being present between the electrodes to which the power supply circuit is connected. The power supply circuit is connected to one of the electrodes at the first site and the electrode at the second site to measure the value of the composite of a contact impedance, a body distal site surrounding composition impedance, and a body composition impedance, these impedances being present between the electrodes to which the power supply circuit is connected. Based on the measured values, the calculating means calculates the value of the body composition impedance.

With the above arrangement, the number of electrodes necessary for the device of the invention can be minimized, compared to the prior art body fat measuring device employing the four terminal method. In addition, the influences of the contact impedances and the body distal site surrounding composition impedances can be thoroughly eliminated to calculate the body composition impedance.

Another alternative of the invention is as follows. The electrodes are provided such that one electrode is disposed so as to contact each of the dermal surface sites which surround hands and feet respectively. The power supply circuit is connected by the impedance measuring means to the electrode in contact with one hand and to the electrode in contact with one foot to measure the value of the composite of a contact impedance, an arm composition impedance, a leg composition impedance and an internal organ impedance, these impedances being present between the electrodes to which the power supply circuit is connected. The power supply circuit is connected to the electrodes in contact with the hands to measure the value of the composite of a contact impedance and an arm composition impedance, these impedances being present between the electrodes to which the power supply circuit is connected. The power supply circuit is connected to the electrodes in contact with the feet to measure the value of the composite of a contact impedance and a leg composition impedance, these impedances being present between the electrodes to which the power supply circuit is connected. The calculating means calculates the value of the internal organ composition impedance, based on the measured values.

With the above arrangement, the measurement of the internal organ composition impedance which previously required eight electrodes can be made with four electrodes. This entails a reduction in the number of wires and circuits, resulting in simplification of the system configuration and cost reduction.

Preferably, the invention further comprises weight measuring means. With this arrangement, the value of weight, which is data necessary for the calculation of the amount of body fat from the body composition impedance, can be measured at the same time with the impedance measurement by the impedance measuring means. This leads to an improvement in the accuracy of the amount of body fat to be finally obtained.

It is also preferable to carry out the measurement of the impedances between the electrodes by the impedance measuring means while weight measurement is made by the weight measuring means, during a transient weight phenomenon state (weight fluctuation state). When the patient steps on the device with his dermal surface sites being brought into contact with the electrodes, the weight measuring means is in its fluctuated state, but a correct impedance measurement is possible. In the above arrangement, the wait time elapsing until the measuring device becomes ready for correct weight measurement is utilized for the impedance measurement so that the value of weight and the amount of body fat can be efficiently measured, while reducing the overall time required for the measurements.

In the invention, when the value of weight measured by the weight measuring means significantly fluctuates, being in an unstable condition, it is preferable to carry out the measurement of the impedances between the electrodes by the impedance measuring means while the weight measurement by the weight measuring means being made. With this arrangement, the impedances between the electrodes can be measured by the impedance measuring means during the wait time elapsing until the transient condition in which the value of weight to be measured by the weight measuring means fluctuates is settled. Therefore, even if a large number of cycles are required for the impedance measurement, in other words, even if it takes a long time to measure the impedances, the prolonged time will not affect the body fat amount measurement carried out simultaneously with the weight value measurement.

In the invention, when the value of weight measured by the weight measuring means does not fluctuate so much, being in a stable condition, it is preferable to interrupt the measurement of the impedances between the electrodes made by the impedance measuring means. Usually, the measurements of the values necessary for the calculation of the body composition impedance is completed by the time the value of weight becomes stable. When the value of weight has become stable, the measurement of the impedances between the electrodes is interrupted and the calculation of the body composition impedance is performed based on the measured values so that the amount of body fat can be output together with the value of weight. Accordingly, the measurement of the impedances between the electrodes can be carried out until the value of weight becomes stable and the calculation of the body composition impedance can be therefore performed with the latest measured values, so that the accuracy of the amount of body fat to be finally obtained can be increased.

In the invention, when the value of weight measured by the weight measuring means does not fluctuate so much, being in a stable condition, it is preferable to interrupt the measurement of the impedances between the electrodes made by the impedance measuring means while only the weight measurement being made. By thus performing the weight measurement continuously, it becomes possible to detect whether the value of weight is in a stable or unstable condition.

DETAILED DESCRIPTION OF THE DRAWINGS

BEST MODE FOR CARRYING OUT THE INVENTION

Referring now to the accompanying drawings, the body fat measuring device of the invention will be hereinafter described according to preferred embodiments.

Figure 1:
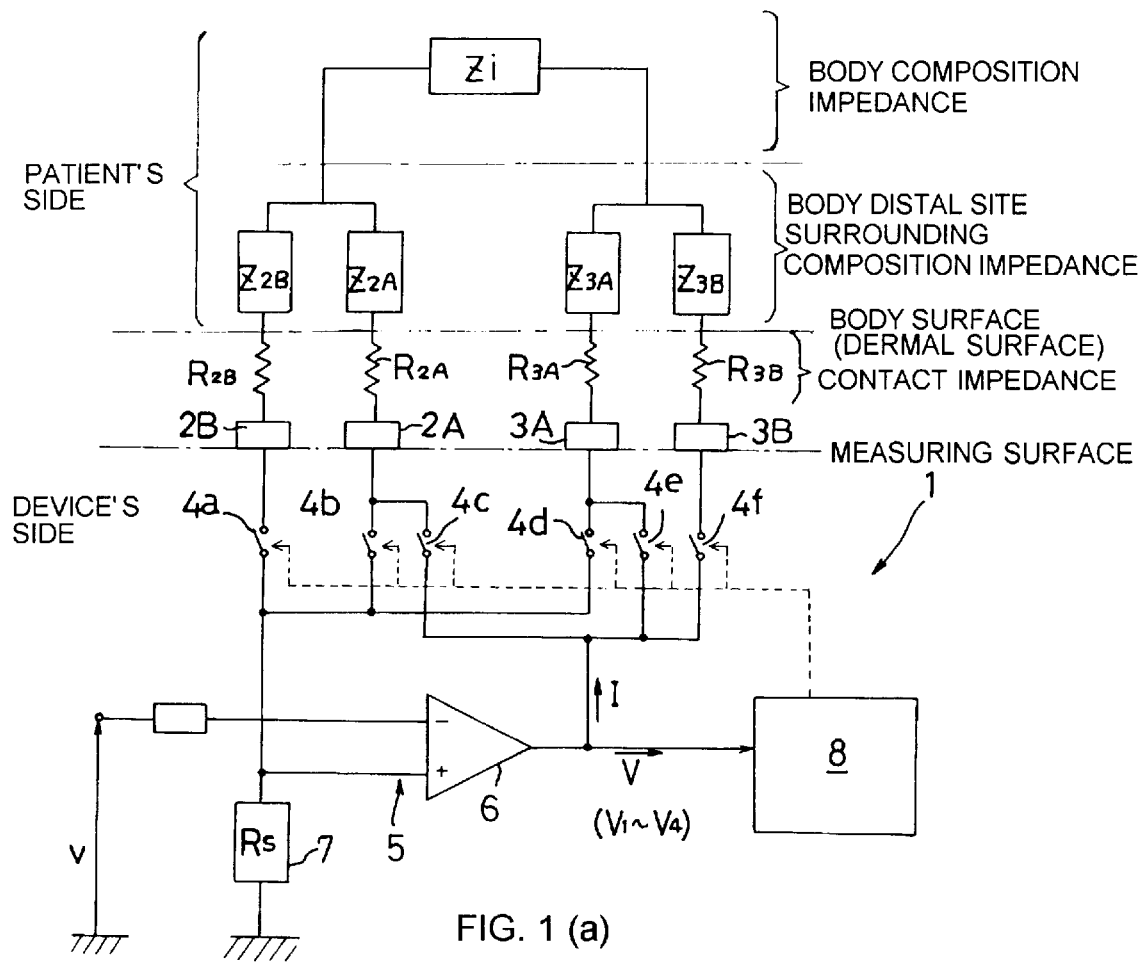
FIG. 1(a) is a circuit diagram showing a body composition impedance measurement circuit in a body fat measuring device according to a first embodiment of the invention.
FIG. 1(b) is an explanatory diagram showing a condition in which a patient-steps on electrodes.
Figure 1:
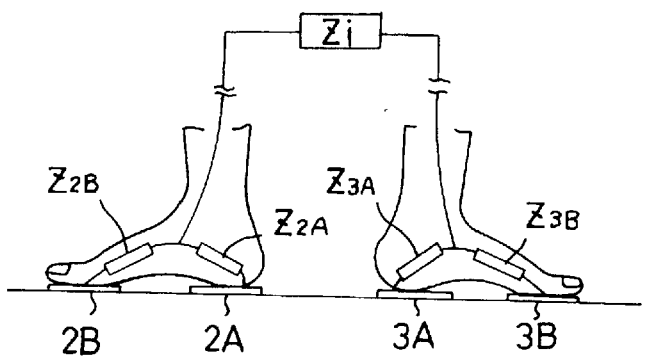

FIG. 1(a) diagrammatically shows a body composition impedance measurement circuit of a body fat measuring device 1 constructed according to a first embodiment of the invention.

In the body fat measuring device 1 of the present embodiment, there are provided two pairs of electrodes (four electrodes) 2A, 2B, 3A, 3B on the top surface thereof. These electrodes 2A, 2B, 3A, 3B are arranged such that a patient steps on each pair of electrodes with one foot. More concretely, the patient puts the respective heals of the feet on the electrodes 2A, 3A and puts the respective tiptoes of the feet on the electrodes 2B, 3B.

FIG. 1(b) diagrammatically shows a condition in which the patient steps on the electrodes 2A, 2B, 3A, 3B. When the feet of the patient touch the electrodes 2A, 2B, 3A, 3B respectively, contact impedances $R_{2A}$, $R_{2B}$, $R_{3A}$ and $R_{3B}$ are generated between the feet and the electrodes 2A, 2B, 3A, 3B. Herein, heel surrounding composition impedances (e.g., impedances each generated in the composition surrounding the heel of each foot) are represented by $Z_{2A}$, $Z_{3A}$, whereas tiptoe surrounding composition impedances (i.e., impedances each generated in the composition surrounding the tiptoe of each hoot) are represented by $Z_{2B}$, $Z_{3B}$. These heel surrounding composition impedances and tiptoe surrounding composition impedances correspond to the body distal site surrounding composition impedances of the invention. In addition, a body composition impedance present between the feet (excluding areas around the distal sites of the feet) is represented by Zi.

The electrodes 2A, 2B, 3A, 3B are connected to a constant current circuit (corresponding to the power supply circuit of the invention) 5 through analog switches 4(4a, 4b; 4c, 4d; and 4e, 4f). The constant current circuit 5 is composed of (i) an operational amplifier 6 which inputs a voltage signal v sent from a non-inverting input terminal and outputs a constant current I and (ii) a reference resistor 7 which is connected to the inverting input terminal of the operational amplifier 6 and which restricts circuit current such that the constant current I is output from the operational amplifier 6. It should be noted that the reference resistor 7 has a stable given value Rs for setting the above constant current I.

The electrodes 2A, 3A, 3B are connected to an output terminal of the operational amplifier 6 through the analog switches 4c, 4e, 4f, respectively. The electrodes 2A, 2B, 3A, 3B are connected to the inverting input terminal of the operational amplifier 6 through the analog switches 4a, 4b, 4d. Further, the output terminal of the operational amplifier 6 is connected to an arithmetic operation control unit 8 (to be described later) within which output voltages V ($V_1$ to $V_4$) from the operational amplifier 6 are stored and the body composition impedance Zi is calculated, based on the output voltages V ($V_1$ to $V_4$).

Figure 2:
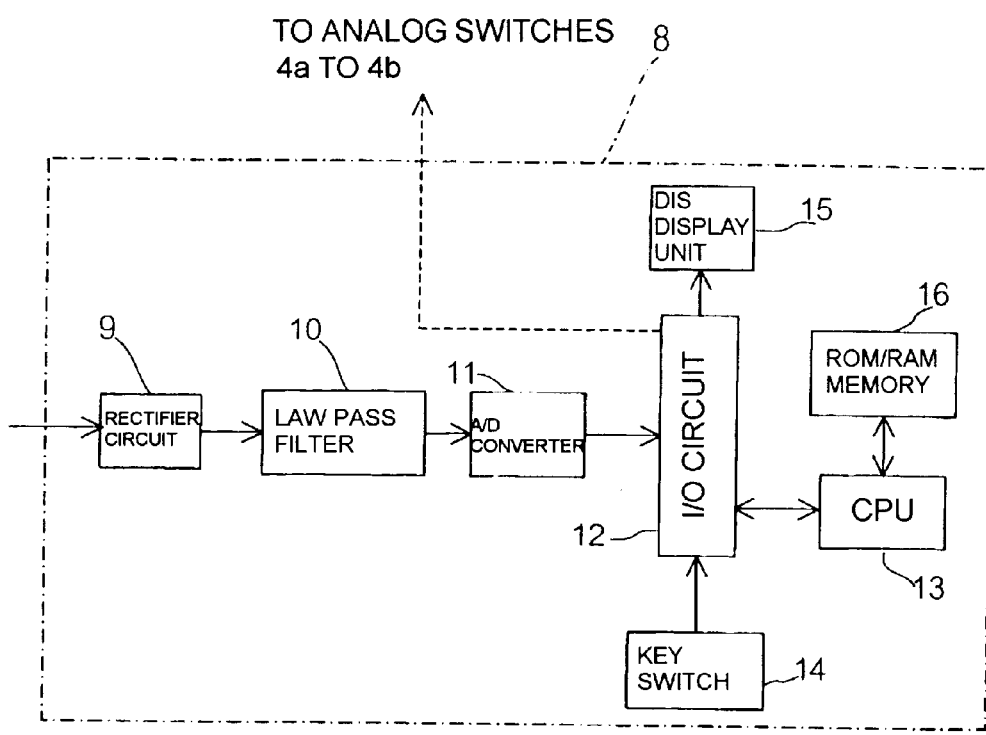
FIG. 2 is a block diagram of an arithmetic operation control unit according to the first embodiment.

FIG. 2 shows a block diagram concretely illustrating the configuration of the arithmetic operation control unit 8. This arithmetic operation control unit 8 is connected to the output terminal of the operational amplifier 6, and comprised of (i) a rectifier circuit 9 for converting an alternate current voltage signal (several tens of KHz) output from the operational amplifier 6 into a direct current, (ii) a low pass filter 10 connected to the rectifier circuit 9 for flattening the voltage signal which has been converted into a direct current, (iii) an A/D converter 11 connected to the low pass filter 10, for digitizing an analog signal, and (iv) an I/O circuit 12 for receiving a digital signal from the A/D converter 11. Connected to the I/O circuit 12 are (i) a CPU 13 for calculating the amount of body fat of a patient based on various pieces of data, (ii) a key switch 14 for inputting personal data (age, height, weight and sex) on the patient, and (iii) a display unit 15 for displaying the amount of body fat (body fat percentage). Connected to the CPU 13 is a ROM/RAM memory (hereinafter referred to as "memory") for storing various pieces of data. Note that the arithmetic operation control unit 8 and CPU 13 of the present embodiment correspond to the impedance measuring means and calculating means of the invention, respectively.

The CPU 13 calculates the body composition impedance Zi based on the output voltages $V_1$ to $V_4$ output from the operational amplifier 6 and calculates the amount of body fat (body fat percentage) based on the thus-calculated body composition impedance Zi and the personal data entered through the key switch 14. The CPU 13 outputs ON/OFF control signals to the analog switches 4a to 4f through the I/O circuit 12, for controlling the ON/OFF states of the analog switches 4a to 4f.

In the body fat measuring device 1 of the above configuration, when the feet of the patient are put on the electrodes 2A, 2B, 3A, 3B, the analog switches 4a to 4f are sequentially switched upon receipt of output signals from the CPU 13 so that the output voltages $V_1$ to $V_4$ from the operational amplifier 6 are input to the arithmetic operation control unit 8. The ON/OFF control of the analog switches 4a to 4f and the output voltages $V_1$ to $V_4$ will be explained below.

The following equation 1 is obtained by measuring the output voltage $V_1$ of the operational amplifier 6 with only the analog switches 4e, 4b turned ON.

$$(R_{3A}+Z_{3A}+Zi+Z_{2A}+R_{2A}+Rs)\cdot I=V_1 \quad \text{(Equation 1)}$$

The following equation 2 is obtained by measuring the output voltage $V_2$ of the operational amplifier 6 with only the analog switches 4f, 4a turned ON.

$$(R_{3B}+Z_{3B}+Zi+Z_{2B}+R_{2B}+Rs)\cdot I=V_2 \quad \text{(Equation 2)}$$

The following equation 3 is obtained by measuring the output voltage $V_3$ of the operational amplifier 6 with only the analog switches 4f, 4d turned ON.

$$(R_{3B}+Z_{3B}+Z_{3A}+R_{3B}+Rs)\cdot I=V_3 \quad \text{(Equation 3)}$$

The following equation 4 is obtained by measuring the output voltage $V_4$ of the operational amplifier 6 with only the analog switches 4c, 4a turned ON.

$$(R_{2A}+Z_{2A}+Z_{2B}+R_{2B}+Rs)\cdot I=V_4 \quad \text{(Equation 4)}$$

These measured output voltages $V_1$, $V_2$, $V_3$, $V_4$ are once respectively stored in the memory 16 of the arithmetic operation control unit 8 and the measured voltages $V_1$, $V_2$, $V_3$, $V_4$ are used in the CPU 13 to calculate the body composition impedance Zi. Specifically, the foregoing equations 1 to 4 are used to calculate the value of Equation 1+Equation 2—(Equation 3+Equation 4). Note that the value of the constant current I is represented by I=v/Rs.

It is accordingly conceivable that the contents of the composition of the distal end of the foot in the case where the conduction route for the constant current I passes through the body does not differ from that in the case where the conduction route goes by way of the electrodes on the back surfaces of the feet. Therefore, if ($Z_{3A}$ of Equation 1)≈($Z_{3A}$ of Equation 3), ($Z_{3B}$ of Equation 2)≈($Z_{3B}$ of Equation 3), ($Z_{2A}$ of Equation 1)≈($Z_{2A}$ of Equation 4), and ($Z_{2B}$ of Equation 2)≈($Z_{2B}$ of Equation 4) hold, $$2Zi·I=V_1+V_2-(V_3+V_4) \text{ and}$$

therefore, $$Zi=\{V_1+V_2-(V_3+V_4)\}/2I.$$

As described in the above equation, only the body composition impedance Zi can be obtained by removing the body distal site composition impedances from the contact impedance and the body inter-distal-site impedance.

Subsequently, based on the body composition impedance Zi and the personal data which have been input beforehand, the amount of body fat (and the body fat percentage) is obtained by the known calculation method within the CPU 13. The amount of body fat (and the body fat percentage) thus obtained is sent to the display unit 15 by way of the I/O circuit 12 to be transmitted to the patient.

According to the first embodiment, the contact impedances $R_{2A}$, $R_{2B}$, $R_{3A}$, $R_{3B}$ and the body distal site surrounding composition impedances $Z_{2A}$, $Z_{3A}$, $Z_{2B}$, $Z_{3B}$ are eliminated and only the stable, body composition impedance Zi is correctly obtained, so that the amount of body fat (and the body fat percentage) can be finally measured with high accuracy.

According to the first embodiment, since the body composition impedance Zi is obtained based on the output voltages $V_1$ to $V_4$ of the operational amplifier 6, there is no need to employ a voltage measurement circuit which is conventionally needed and as a result, the system configuration can be simplified, leading to cost reduction.

Figure 3:
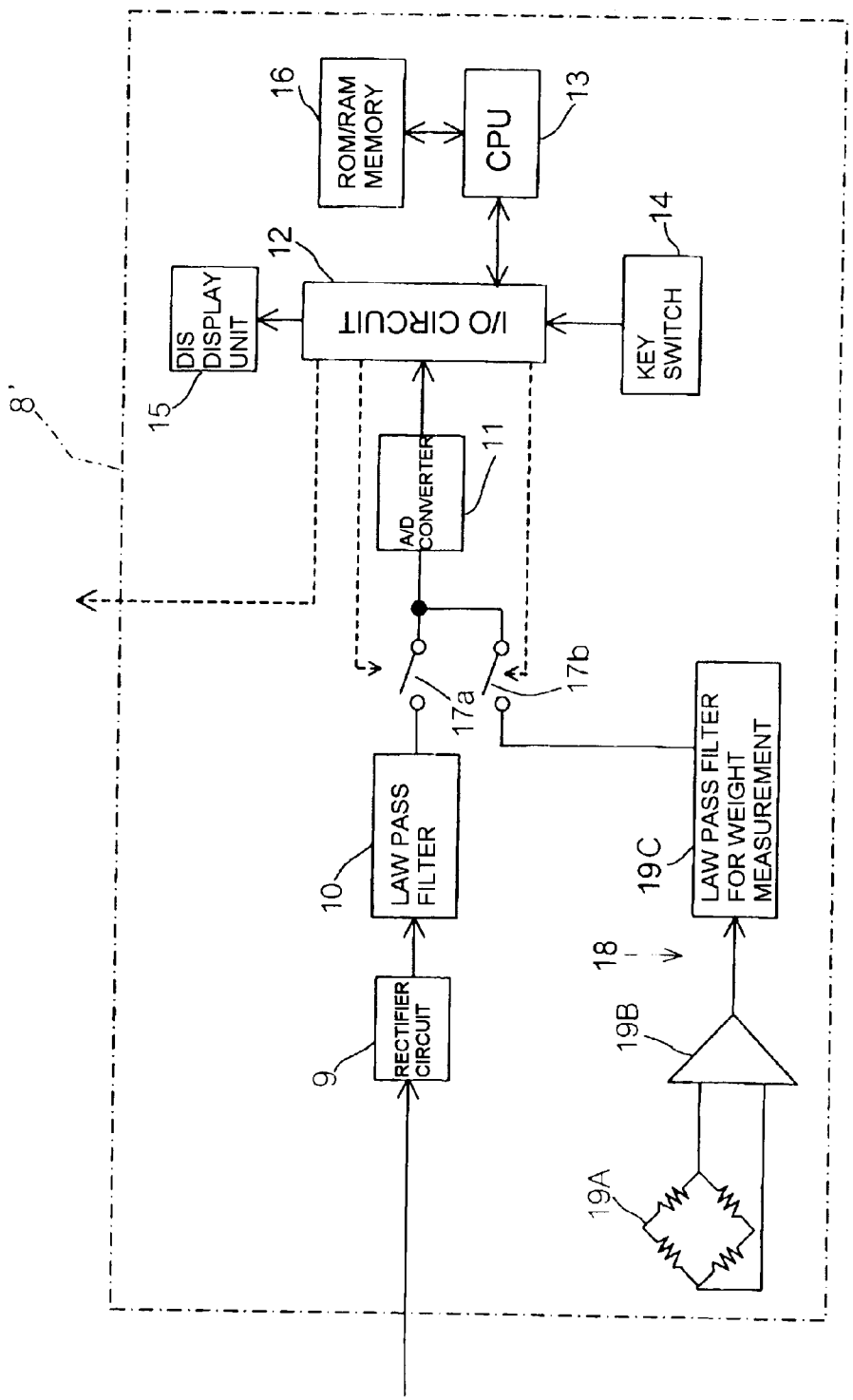
FIG. 3 is a block diagram of the arithmetic operation control unit into which a weight measurement circuit is incorporated.

While the arithmetic operation control unit 8 according to the first embodiment is designed to measure only the amount of body fat, it may be arranged as shown in FIG. 3, in which an analog switch 17a is provided between the low pass filter 10 and the A/D converter 11 and a weight measurement circuit (which corresponds to the weight measuring means of the invention) 18 is coupled to the back of the analog switch 17a through an analog switch 17b so that the weight of the patient can be measured simultaneously with the measurement of the amount of body fat. In this case, it is unnecessary to input the value of weight as personal data by the key switch 14. In the example shown in FIG. 3, the weight measurement circuit 18 is comprised of a weight sensor (which is a load cell in this embodiment) 19A, an operational amplifier 19B and a low pass filter 19C for weight measurement. Concretely, an output signal from the weight sensor 19A is amplified by the operational amplifier 19B and passes through the low pass filter for weight measurement 19C to be flattened. Then, the output signal is input to the CPU 13 by way of the aforesaid A/D converter 11 and I/O circuit 12. It should be noted that, a weight difference threshold value Wa used for determining that a weight value is in a stable condition, a weight difference threshold value Wb used for determining that a weight value is in an unstable condition, and a lowest weight value Wc used for displaying a body fat percentage are respectively set in the CPU 13. Herein, the threshold values Wb and Wa satisfies Wb>Wa.

Figure 4:
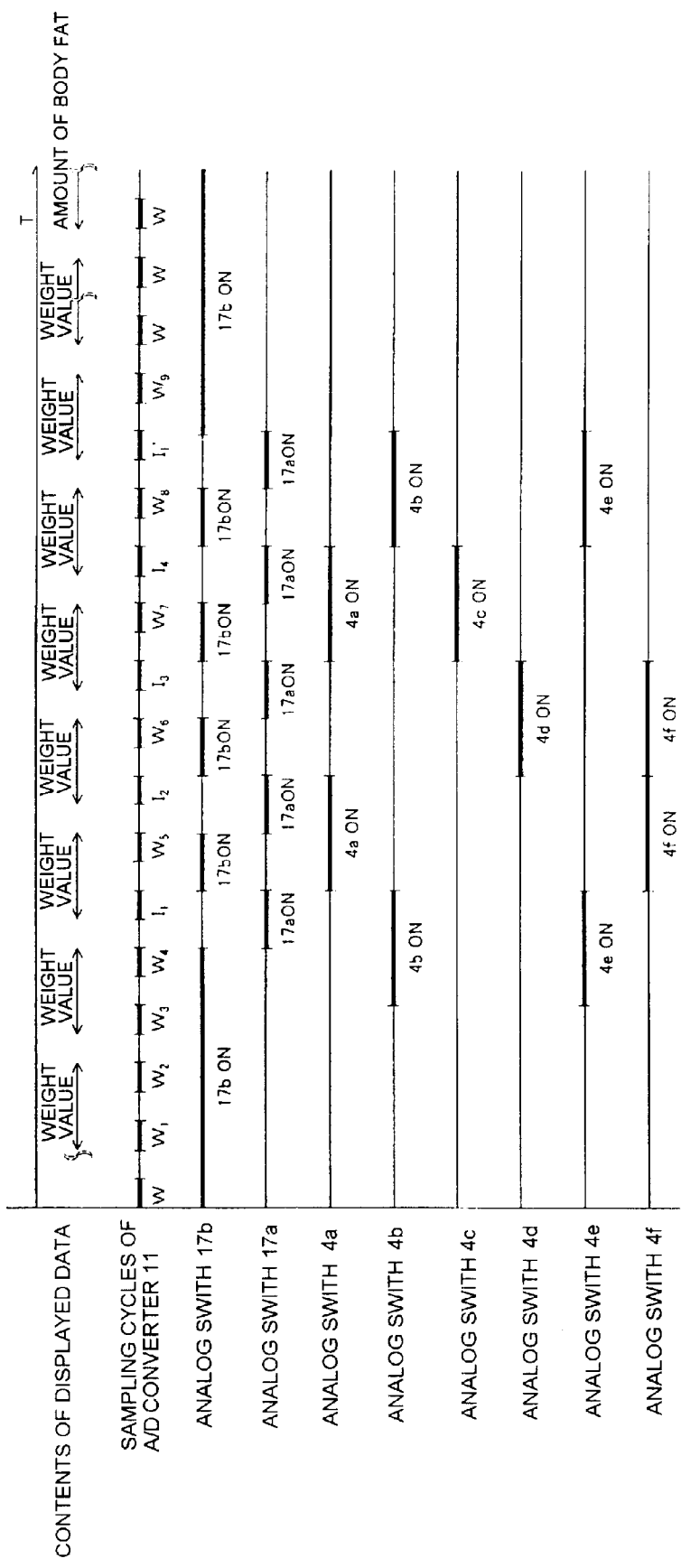
FIG. 4 is an explanatory diagram illustrating one example of a measurement sequence for body fat and weight.

FIG. 4 is an explanatory diagram showing one example of a measurement sequence for body fat and weight in an arithmetic operation control unit 8'. In the CPU 13 of the arithmetic operation control unit 8', the ON/OFF control of the display unit 15, the A/D converter 11 and the analog switches 17a, 17b and 4a to 4f is executed based on the measurement sequence. This measurement sequence represents the contents of data displayed on the display unit 15, the sampling cycles of the A/D converter 11, the ON states of the analog switches 17b, 17a and 4a to 4f in this order from above.

Codes W ($W_1$ to $W_9$) in FIG. 4 represent the cycles in which the A/D converter 11 samples weight signals, whereas codes I ($I_1$ to $I_4$) represent the cycles in which the A/D converter 11 samples output voltage signals ($V_1$ to $V_4$) released from the operational amplifier 6.

The output signal (analog weight value) of the weight sensor 19A is A/D converted through the amplifier 19B and the low pass filter for weight measurement 19C to be input to the I/O circuit 12. At the same time, a stability judgement for determining whether the value of weight is stable is made by comparing newly and sequentially input weight values with previously input weight values. The weight data used for the stability judgement may be based on, for example, the comparison between the average of a specified number of new input data pieces and the average of the specified number of previous input data pieces or alternatively may be based on the comparison between a single new data piece and a single previous data piece. If the difference between the latest weight value and the preceding weight value immediately before the latest one is smaller than the aforesaid weight difference threshold value Wa, it is then determined that the weight value is in a stable condition. If the weight value is smaller than the aforesaid lowest weight value Wc, it is then determined that weight measurement is not made so that impedance measurement, that is, body fat measurement will not be made.

When the patient steps on the body fat measuring device 1 with his feet being put on the electrodes 2A, 2B and 3A, 3B, respectively, the value output from the weight sensor 19A significantly changes because of the load of the weight, and it is then judged that the body fat measuring device is ready for weight measurement and body fat measurement. Herein, if the difference between the latest weight value and the weight value immediately before the latest one is greater than the weight difference threshold value Wb, it is determined in the above-described stability judgment that the weight value is in its unstable condition and the patient has stepped on the measuring device 1, and then, the weight of the patient as well as the body composition impedance Zi is measured in the following way. By setting the weight difference threshold values Wa, Wb so as to satisfy Wb>Wa as mentioned earlier, the measurement mode is not fluctuated, in an oscillating manner by the value of weight which is in the vicinity of the threshold points for judgement. When the patient steps off the measuring device 1 or moves on the measuring device 1, it is determined that the value of weight is in its unstable condition so that the body composition impedance measurement for body fat measurement starts.

When the patient has stepped on the measuring device 1 and if the difference between a weight value obtained in a first sampling cycle $W_1$ by the A/D converter 11 and a weight value obtained in a second sampling cycle $W_2$ is greater than the weight difference threshold value Wb so that the unstable state of the value of weight is determined, only the analog switches 4e, 4b are turned ON after completion of a third sampling cycle $W_3$ by the A/D converter 11 (i.e., after completion of the A/D converting operation). Further, upon completion of a fourth sampling cycle $W_4$ by the A/D converter 11, the analog switch 17b is turned OFF while the analog switch 17a is turned ON so that the body composition impedance measurement, that is, a sampling cycle $I_1$ of the body composition impedance is started and the output voltage signal $V_1$ from the operational amplifier 6 is A/D converted by the A/D converter 11. With a timing a little before the sampling cycle $I_1$ by the A/D converter 11, the output voltage signal $V_1$ is input to the low pass filter 10 to be flattened. When the counted time approaches the sampling cycle $I_1$, the analog switch 17a is turned ON to A/D convert the signal $V_1$ whereby a stable impedance signal is taken in the arithmetic operation circuit. The output voltage signal $V_1$, which has been A/D converted in the above sampling cycle $I_1$, is stored in the memory 16 via the I/O circuit 12.

After the sampling cycle $I_1$ has been subsequently completed, the analog switch 17b is again turned ON (while the analog switch 17a is turned OFF) and the weight measurement circuit 18 is connected to the A/D converter 11, while only the analog switches 4f, 4a are turned ON so that the output voltage signal $V_2$ from the operational amplifier 6 is supplied to the low pass filter 10 to be flattened. Meanwhile, weight signals from the weight sensor 19A of the weight measurement circuit 18 are sequentially input to the low pass filter for weight measurement 19C to be A/D converted by the A/D converter 11 in a sampling cycle $W_5$.

After completion of the sampling cycle $W_5$ for sampling the weight signals by the A/D converter 11, the analog switch 17a is turned ON (while the analog switch 17b is turned OFF), thereby starting a sampling cycle $I_2$ for the body composition impedance and the output voltage signal $V_2$ flattened by the low pass filter 10 is A/D converted. In this way, the output voltage signal $V_2$ converted in the sampling cycle $I_2$ is stored in the memory 16 via the I/O circuit 12.

After completion of the sampling cycle $I_2$, the analog switch 17b is again turned ON (while the analog switch 17a is turned OFF), thereby connecting the weight measurement circuit 18 to the A/D converter 11, while only the analog switches 4f, 4d are turned ON so that the output voltage signal $V_3$ from the operational amplifier 6 is supplied to the low pass filter 10 to be flattened. In the mean time, weight signals from the weight sensor 19A of the weight measurement circuit 18 are sequentially input to the low pass filter for weight measurement 19C and A/D converted by the A/D converter 11 in a sampling cycle $W_6$.

After completion of the sampling cycle $W_6$ for sampling the weight signals by the A/D converter 11, the analog switch 17a is turned ON (while the analog switch 17b is turned OFF) to start a sampling cycle $I_3$ for the body composition impedance, and the output voltage signal $V_3$ flattened by the low pass filter 10 is A/D converted. In this way, the output voltage signal $V_3$ converted in the sampling cycle $I_3$ is stored in the memory 16 by way of the I/O circuit 12.

After the sampling cycle $I_3$ has been subsequently completed, the analog switch 17b is again turned ON (while the analog switch 17a is turned OFF) thereby connecting the weight measurement circuit 18 to the A/D converter 11. Only the analog switches 4c, 4a are turned ON, thereby supplying the output voltage signal $V_4$ from the operational amplifier 6 to the low pass filter 10 for flattening. Meanwhile, weight signals from the weight sensor 19A of the weight measurement circuit 18 are sequentially input to the low pass filter for weight measurement 19C and A/D converted by the A/D converter 11 in a sampling cycle $W_7$.

After completion of the sampling cycle $W_7$ for sampling the weight signals by the A/D converter 11, the analog switch 17a is turned ON (while the analog switch 17b is turned OFF) whereby a sampling cycle $I_4$ for the body composition impedance is started and the output voltage signal $V_4$ which has been flattened by the low pass filter 10 is A/D converted. The output voltage signal $V_4$ which has been converted in the sampling cycle $I_4$ is stored in the memory 16 by way of the I/O circuit 12. In this way, the output voltages $V_1$ to $V_4$ necessary for the calculation of the body composition impedance Zi are stored in the memory 16.

After the sampling cycles $W_5$ to $W_7$ for sampling the weight signals have been completed, a stability judgement is made for each of the weight values. Even when the output voltages ($V_1$ to $V_4$) necessary for the calculation of the body composition impedance Zi have been stored in the memory 16, if a weight value is in an unstable condition (i.e., the difference between an obtained weight value and the preceding weight value is greater than the weight difference threshold value Wb), the analog switches 17a, 17b are continued to be alternately switched to make weight measurement and body composition impedance measurement.

Specifically, if it is determined that the difference between the weight value obtained in the weight signal sampling cycle $W_8$ carried out after completion of the sampling cycle $I_4$ and the weight value obtained in the preceding sampling cycle $W_7$ is greater than the weight difference threshold value Wb (i.e., the weight value is in an unstable condition), the operation of the measuring device is again switched to the body composition impedance measurement mode to start an impedance sampling cycle $I_1'$. In this sampling cycle $I_1'$, the output voltage signal $V_1$ from the operational amplifier 6 is A/D converted to be stored in the memory 16, while the output voltage signal $V_1$ which has been previously stored in the memory 16 is updated. If it is determined that the difference between the weight value obtained in the weight signal sampling cycle $W_9$ carried out after completion of the sampling cycle $I_1'$ and the weight value obtained in the preceding weight value sampling cycle $W_8$ is smaller than the weight difference threshold value Wa (i.e., stable condition), the body composition impedance measurement is interrupted. After stability judgements for the weight values have been made in this way, the body composition impedance Zi is calculated by the CPU 13, using the output signals $V_1$ to $V_4$ stored in the memory 16, while the amount of body fat (body fat percentage) is calculated from the body composition impedance Zi and the personal data.

If a weight value is determined to be in a stable condition and greater than the lowest weight value Wc, the weight value (measured weight value) is displayed on the display unit 15 until a specified time elapses. After the specified time has elapsed, the amount of body fat (body fat percentage) calculated in the CPU 13 is displayed on the display unit 15. After the specified time has further elapsed, the weight value is again displayed on the display unit 15. After that, the weight value and the amount of body fat are repeatedly displayed every elapse of the specified time as far as the weight value stability judgement is continued. During the time when the weight value stability judgement continues, only the weight value measurement is continuously executed and the stability judgement is always carried out. Before the stability of a weight value is determined, the weight values obtained in the sampling cycles $W_1$ to $W_8$ are sequentially displayed on the display unit 15 since it is necessary to inform the patient of sequential changes in the value of weight in a transient condition.

If the patient has, for instance, stepped out of the measuring device 1 so that it is determined that the value of weight is in an unstable condition, the weight value measurement and the body composition impedance measurement are alternately repeated again. Since the value of weight is lower than the lowest weight value Wc even if the stable condition is determined, only the value of weight is displayed on the display unit 15. If the patient has moved on the measuring device 1 with a determination that the value of weight is in an unstable condition, when the stability is later determined again, the value of weight is greater than the lowest weight value Wc, and therefore the weight value and the amount of body fat are alternately displayed on the display unit 15.

In the above measurement sequence, after a series of output voltage signals $V_1$ to $V_4$ sent from the operational amplifier 6 is stored in the memory 16, the measurement of the body composition impedance is interrupted at the moment when the stability of the value of weight is determined, but if storage of a series of output voltage signals $V_1$ to $V_4$ has not been completed yet after determination of the stable condition, a series of output voltage signals $V_1$ to $V_4$ is stored in the memory 16 and thereafter the body composition impedance measurement is interrupted.

According to the measurement sequence, when the patient steps on the top surface of the measuring device 1 with his feet put on the electrodes 2A, 2B, 3A, 3B, a quite long time elapses since the value of weight is in an oscillating condition until the value of weight becomes stable so that a correct weight value can be obtained. However, since the feet of the patient are fixedly attached to the electrodes 2A, 2B, 3A, 3B and therefore the measuring device 1 is ready for correct body composition impedance measurement, this wait time can be utilized for measuring the body composition impedance simultaneously with the weight measurement. Accordingly, the measuring device 1 comes into the condition in which the body composition impedance Zi can be calculated, by the time the value of weight becomes stable, so that even if many cycles are required for the calculation of the body composition impedance, the time required for the cycles does not affect the measurements of the final values of weight value and body fat amount. Preferably, after the value of weight becomes stable, in other words, after the difference between the latest and preceding weight values falls in the range less than the weight difference threshold value Wa, a correct weight value is displayed. In addition, since a large volume of weight data is required at the shortest possible time intervals in filtering calculation such as average calculation in order to reduce flickering of a displayed weight value as much as possible, it is preferable to make only a weight measurement every time.

Next, a body fat measuring device 20 according to a second embodiment of the invention will be explained. The body fat measuring device 20 of the second embodiment does not basically differ from the body fat measuring device 1 of the first embodiment except the configuration of the body composition impedance measurement circuit. Therefore, only the configuration of the body composition impedance measurement circuit 21 peculiar to the second embodiment will be explained and a detailed explanation on other parts common to the first and second embodiments will be omitted.

Figure 5:
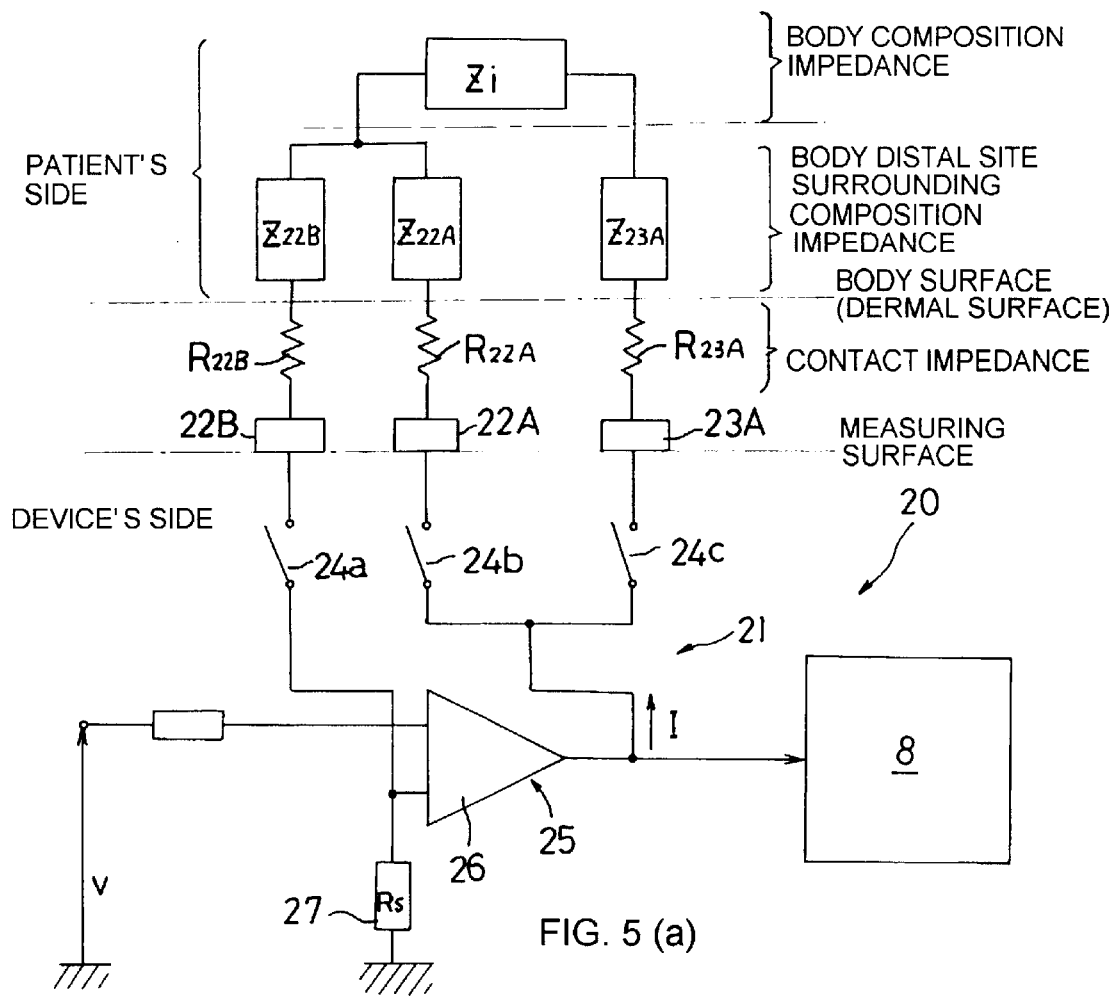
FIG. 5(a) is a circuit diagram showing a body composition impedance measurement circuit in a body fat measuring device according to a second embodiment of the invention.
FIG. 5(b) is an explanatory diagram showing a condition in which a patient steps on electrodes.
Figure 5:
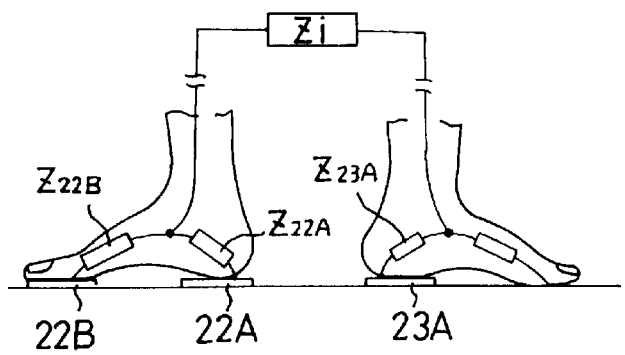

FIG. 5(a) is a circuit diagram showing the body composition impedance measurement circuit 21 constructed according to the second embodiment. The body fat measuring device 20 has three electrodes 22A, 22B and 23A on the top surface thereof and is designed such that the patient steps on the electrodes 22A, 22B with one foot and on the electrode 23A with the other foot. More specifically, the patient puts hits heels on the electrodes 22A, 23A and his tiptoe on the electrode 22B.

FIG. 5(b) diagrammatically illustrates a condition in which the patient steps on the electrodes 22A, 22B and 23A. Generated between the feet of the patient and the respective electrodes 22A, 22B, 23A are contact impedances $R_{22A}$, $R_{22B}$, $R_{23A}$. There are generated, around the backs of the feet, body distal site surrounding composition impedances $Z_{22A}$, $Z_{22B}$, $Z_{23A}$. A body composition impedance to be measured that is present between the feet is represented by Zi in FIG. 5(b).

The electrodes 22B, 22A, 23A are connected to a constant current circuit 25 through analog switches 24a, 24b, 24c, respectively. Like the first embodiment, this constant current circuit 25 is comprised of (i) an operational amplifier 26 which inputs a voltage signal v sent from a non-inverting input terminal and outputs a constant current I and (ii) a reference resistor 27 which is connected to the inverting input terminal of the operational amplifier 26 and which restricts circuit current such that the constant current I is output from the operational amplifier 26. Note that the reference resistor 27 has a stable given value Rs for setting the constant current I.

The electrodes 22A, 23A are connected to the output terminal of the operational amplifier 26 through the analog switches 24b, 24c respectively, and the electrode 22B is connected to the inverting input terminal of the operational amplifier 26 through the analog switch 24a. The output terminal of the operational amplifier 26 is connected to the arithmetic operation control unit 8.

In the body fat measuring device 20 comprising the body composition impedance measurement circuit 21 of the above configuration, while the patient's feet are placed on the electrodes 22A, 22B, 23A, the analog switches 24a to 24c are sequentially switched upon receipt of output signals supplied from the CPU 13 of the arithmetic operation control unit 8 so that the output voltages $V_5$, $V_6$ from the operational amplifier 26 are input to the arithmetic operation control unit 8. The ON/OFF control of the analog switches 24a to 24c and the output voltages $V_5$, $V_6$ will be described below.

By measuring the output voltage $V_5$ of the operational amplifier 26 with only the analog switches 24a, 24c turned ON, the following equation 5 is obtained.

$$(R_{23A}+Z_{23A}+Zi+Z_{22B}+R_{22B}+Rs) \cdot I = V_5 \quad \text{(Equation 5)}$$

By measuring the output voltage $V_6$ of the operational amplifier 26 with only the analog switches 24a, 24c turned ON, the following equation 6 is obtained.

$$(R_{22A}+Z_{22A}+Z_{22B}+R_{22B}+Rs) \cdot I = V_6 \quad \text{(Equation 6)}$$

The measured output voltages $V_5$, $V_6$ are once stored in the memory 16 of the arithmetic operation control unit 8. In the CPU 13, calculation of the body composition impedance Zi is performed, using the measured voltages $V_5$, $V_6$. Specifically, the value of Equation 6 is subtracted from the value of Equation 5 (Equation 5–Equation 6). Note that the constant current I is represented by I=v/Rs. Accordingly, the contact impedance $R_{22A} \approx$ the contact impedance $R_{23A}$ holds and it is conceivable that the contents of the composition in the right foot do not differ from that of the left foot and that the contents of the composition in cases where the current conduction route goes through the body do not differ from that in cases where the current conduction route goes between the electrodes on the backs of the feet. Therefore, if $Z_{23A}$ of Equation $5 \approx Z_{22A}$ of Equation 6 and $Z_{22B}$ of Equation $5 \approx Z_{22B}$ of Equation 6 hold, $Zi \cdot I = V_5 - V_6$ and, therefore, $Zi = (V_5 - V_6)/I$. By performing such calculations, the body composition impedance Zi can be obtained.

In the CPU 13, based on the body composition impedance Zi and personal data which have been input beforehand, the amount of body fat (body fat percentage) is obtained using the known calculation method. The amount of body fat (body fat percentage) thus obtained is displayed on the display unit 15 via the I/O circuit 12 to be transmitted to the patient.

As factors that cause an error in measuring the body composition impedance Zi, there are (i) the difference between the measured values $R_{22A}$ and $R_{23A}$; (ii) the difference between the measured values $Z_{23A}$ of Equation 5 and $Z_{22A}$ of Equation 6; and (iii) the difference between the measured values $Z_{22B}$ of Equation 5 and $Z_{22B}$ of Equation 6. However, the difference between $R_{22A}$ and $R_{23A}$ can be solved by making the electrodes 22A, 23A larger. Also, the difference between $Z_{23A}$ and $Z_{22A}$ and the difference between $Z_{22B}$ and $Z_{22B}$ are practically negligible, since the difference between $Z_{23A}$ and $Z_{22A}$ and the difference between $Z_{22B}$ and $Z_{22B}$ are smaller than the impedance of the body to be measured when taking the fact into account that there is virtually no difference between their conduction routes. Therefore, the body composition impedance unaffected by the contact impedances and the body distal site surrounding composition impedances can be obtained by the above calculation.

According to the second embodiment, substantially the same effect as that of the first embodiment can be attained and the condition of a body surface to be measured during the short measurement time is substantially the same as that of the first embodiment. Therefore, on assumption that the contact impedances at all the sites have the same value and the body distal site surrounding composition impedances at all the sites have the same value, a pair of electrodes 22A, 22B are provided for only one representative site and the other sites are each provided with one electrode 23A to enable body impedance measurement. With this arrangement, the number of electrodes can be reduced, entailing a simplified system configuration and, in consequence, cost reduction.

In cases where the device of the second embodiment is applied to an impedance measurement made at a cross section of the trunk of a human body for instance, the reduced number of electrodes leads to a reduction in the time required for electrode attachment. Concretely, the measurement described by the above Equation 6 is made at the site where a pair of electrodes are provided and the measurement described by the above Equation 5 is made at the other n sites. If the contact impedances at all the sites have the same value and the body distal site surrounding composition impedances at all the sites have the same value, the impedances at the n sites can be obtained by subtracting the value of Equation 6 from the value of Equation 5, these values having been obtained by measurements at each site.

Next, a body fat measuring device 30 constructed according to a third embodiment of the invention will be explained. The body fat measuring device 30 of the third embodiment does not basically differ from the body fat measuring device 1 of the first embodiment except the configuration of the body composition impedance measurement circuit. Therefore, only the configuration of the body composition impedance measurement circuit 31 peculiar to the third embodiment will be explained and a detailed explanation on other parts common to the first and third embodiments will be omitted.

Figure 6:
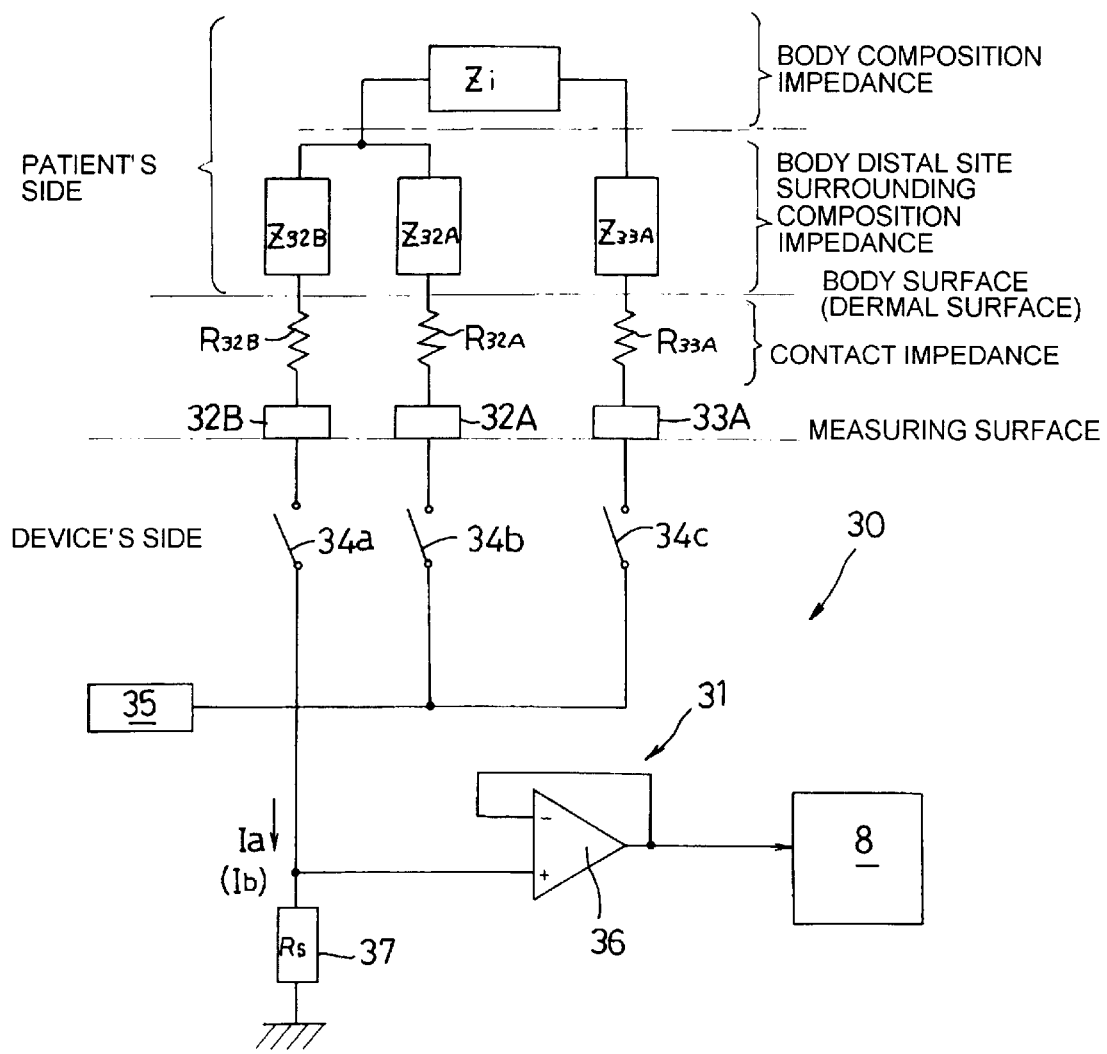
FIG. 6 is a circuit diagram showing a body composition impedance measurement circuit in a body fat measuring device according to a third embodiment of the invention.

FIG. 6 is a circuit diagram showing the body composition impedance measurement circuit 31 constructed according to the third embodiment. This body fat measuring device 30 has three electrodes 32A, 32B and 33A on the top surface thereof and is designed such that the patient steps on the electrodes 32A, 32B with one foot and on the electrode 33A with the other foot. More specifically, the patient places his heels on the electrodes 32A, 33A and his tiptoe on the electrode 32B.

Contact impedances $R_{32A}$, $R_{32B}$, $R_{33A}$ are generated between the respective feet of the patient and the respective electrodes 32A, 32B, 33A, whereas body distal site surrounding composition impedances which present much around the backs of the feet $Z_{32A}$, $Z_{32B}$, $Z_{33A}$ are generated. Note that a body composition impedance to be measured that is present between the feet is represented by Zi in FIG. 6.

The electrodes 32A, 33A are connected to a voltage source (which corresponds to the power supply circuit of the invention) 35 for supplying a constant voltage V through analog switches 34b, 34c respectively. The electrode 32B is connected to a reference resistor (Rs) 37 that is coupled to the non-inverting terminal of an operational amplifier 36 through an analog switch 34a. The output terminal of the operational amplifier 36 is connected to the arithmetic operation control unit 8.

In the body fat measuring device 30 comprising the body composition impedance measurement circuit 31 of the above configuration, while the patient's feet are placed on the electrodes 32A, 32B, 33A, the analog switches 34a to 34c are sequentially switched upon receipt of output signals from the CPU 13 of the arithmetic operation control unit 8 so that output signals from the operational amplifier 36 are input to the arithmetic operation control unit 8. The ON/OFF control of the analog switches 34a to 34c and the output voltages $V_5$, $V_6$ will be described below.

Only the analog switches 34a, 34c are turned ON. Where the current flowing in the circuit at that time is Ia and the voltage generated across the reference resistor 37 at that time is Va, the following equation holds.

$$(R_{33A}+Z_{33A}+Zi+Z_{32A}+R_{32A}+Rs)\cdot Ia=V$$

The above equation can be rewritten as follows with Ia=Va/Rs.

$$R_{33A}+Z_{33A}+Zi+Z_{32A}+R_{32A}=(V-Va)/Ia=\{(V-Va)/Va\}\cdot Rs=L1 \quad \text{(Equation 7)}$$

Only the analog switches 34a, 34b are turned ON. Where the current flowing in the circuit at that time is Ib and the voltage generated across the reference resistor 37 at that time is Vb, the following equation holds.

$$(R_{32B}+Z_{32B}+Z_{32A}+R_{32A}+Rs)\cdot Ib=V$$

The above equation can be rewritten as follows with Ib=Vb/Rs.

$$R_{32B}+Z_{32B}+Z_{32A}+R_{32A}=(V-Vb)/Ib=\{(V-Vb)/Vb\}\cdot Rs=L2 \quad \text{(Equation 8)}$$

The contact impedance $R_{32A}$≈the contact impedance $R_{33A}$ holds like the foregoing case, and it is conceivable that the contents of the composition in the right foot do not differ from that of the left foot and that the contents of the composition in cases where the current conduction route goes through the body do not differ from that in cases where the current conduction route goes between the electrodes on the backs of the feet. Therefore, if $Z_{33A}$ of Equation 7≈$Z_{32A}$ of Equation 8 and $Z_{32B}$ of Equation 7≈$Z_{32B}$ of Equation 8 hold, the body composition impedance Zi can be obtained by subtracting Equation 8 from Equation 7 (Zi=L1−L2).

Substantially the same effect as those of the foregoing embodiments can be obtained by the third embodiment. The third embodiment is particularly useful in cases where the contact impedance is so high that the first and second embodiments cannot be applied because the operational amplifier constituting the constant current circuit is saturated.

While three electrodes 32A, 32B, 33A are provided and these electrodes are coupled to the body composition impedance measurement circuit 31 in the third embodiment, the invention is not limited to this but may be arranged differently. For instance, there may be provided four electrodes which are coupled, through six analog switches respectively, to a body composition impedance measurement circuit to which constant voltage is applied. In this case, the ON/Off control of the analog switches is substantially similar to that of the first embodiment and the body composition impedance Zi can be calculated based on Equations 7 and 8.

Figure 7:
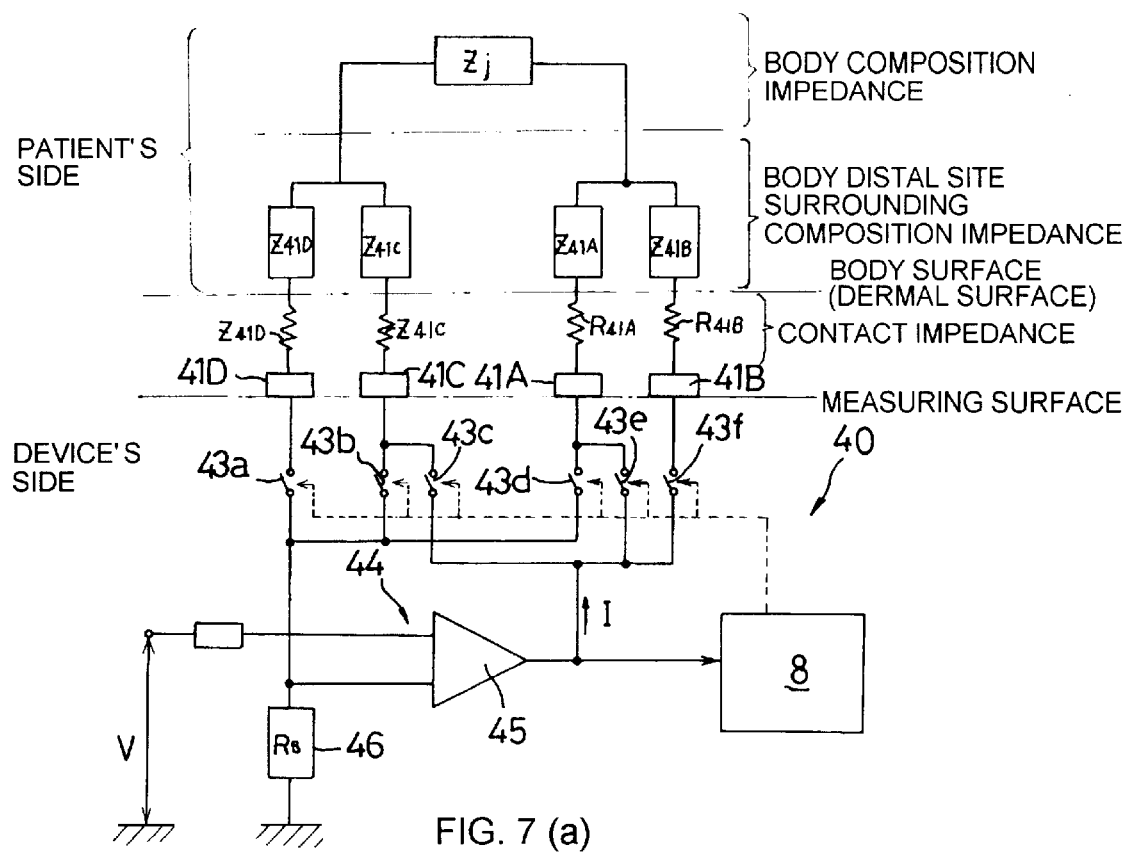
FIG. 7(a) is a circuit diagram showing a body composition impedance measurement circuit in a body fat measuring device according to a fourth embodiment of the invention.
FIG. 7(b) is an explanatory diagram illustrating composition impedances in a human body.
Figure 7B:
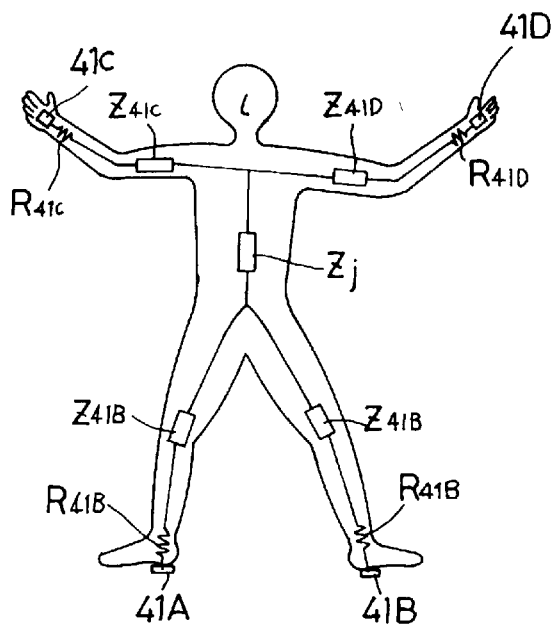

Next, a body fat measuring device 40 according to a fourth embodiment will be described. FIG. 7(a) is a circuit diagram showing a body composition (internal organ composition) impedance measurement circuit of the body fat measuring device of the fourth embodiment. FIG. 7(b) diagrammatically illustrates body composition impedances. The body fat measuring device 40 of the present embodiment has electrodes 41A, 41B on which the feet of the patient are to be respectively placed and electrodes 41C, 41D which are to be respectively grasped by the hands of the patient. The electrodes 41D, 41C, 41A, 41B are respectively connected to a constant current circuit 44 through analog switches 43a, 43b, 43c, 43d, 43e, 43f, the constant current circuit 44 having the same configuration as that of the first embodiment. The output terminal of an operational amplifier 45 that constitutes the constant current circuit 44 is connected to the arithmetic operation control unit 8. This arithmetic operation control unit 8 is the same as that of the first embodiment in configuration and therefore, an explanation thereof will be omitted.

The electrodes 41C, 41A, 41B are connected to the output terminal of the operational amplifier 45 through the analog switches 43c, 43e, 43f. The electrodes 41D, 41C, 41A are connected to the inverting input terminal of the operational amplifier 45 through the analog switches 43a, 43b, 43d, respectively. The inverting output terminal of the operational amplifier 45 is connected to a reference resistor 46 for limiting circuit current such that the constant current I is output from the operational amplifier 45. It should be noted that the reference resistor 46 has a stable given value Rs for setting the constant current I.

The body composition impedance of the patient will be explained below. In the fourth embodiment, since the electrodes 41A, 41B, 41C, 41D are in contact with the hands and feet of the patient respectively, contact impedances $R_{41A}$, $R_{41B}$, $R_{41C}$, $R_{41D}$ are generated between the hands and feet of the patient and the electrodes 41A, 41B, 41C, 41D respectively, whereas body composition impedances $Z_{41A}$, $Z_{41B}$, $Z_{41C}$, $Z_{41D}$ are generated in the right foot, left foot, right arm and left arm respectively. In FIG. 7, the impedance of an internal organ composition to be measured, that is, the internal organ composition impedance is represented by Zj.

In the body fat measuring device 40 of the above configuration, while the right foot and left foot of the patient are placed on the electrodes 41A, 41B respectively and the electrodes 41C, 41D are grasped by the right and left hands, respectively, the analog switches 43a, 43b, 43c, 43d, 43e, 43f are sequentially switched through the ON/OFF control by the CPU 13 so that output voltages $V_9$ to $V_{12}$ released from the operational amplifier 45 are input to the arithmetic operation control unit 8. The ON/OFF control of the analog switches 43a to 43f and the output voltages $V_9$ to $V_{12}$ will be explained below.

With only the analog switches 43b, 43e turned ON, the output voltage $V_9$ of the operational amplifier 45 is measured, thereby obtaining the following equation.

$$(R_{41A}+Z_{41A}+Zj+Z_{41C}+R_{41C}+Rs)\cdot I=V_9 \quad \text{(Equation 9)}$$

With only the analog switches 43a, 43f turned ON, the output voltage $V_{10}$ of the operational amplifier 45 is measured, thereby obtaining the following equation.

$$(R_{41B}+Z_{41B}+Zj+Z_{41D}+R_{41D}+Rs)\cdot I=V_{10} \quad \text{(Equation 10)}$$

With only the analog switches 43a, 43c turned ON, the output voltage $V_1$, of the operational amplifier 45 is measured, thereby obtaining the following equation.

$$(R_{41C}+Z_{41C}+Z_{41D}+R_{41D}+Rs)\cdot I=V_1 \quad \text{(Equation 11)}$$

With only the analog switches 43d, 43f turned ON, the output voltage $V_{12}$ of the operational amplifier 45 is measured, thereby obtaining the following equation.

$$(R_{41B}+Z_{41B}+Z_{41A}+R_{41A}+Rs)\cdot I=V_{12} \quad \text{(Equation 12)}$$

These output voltages $V_9$ to $V_{12}$ are once stored in the memory 16 of the arithmetic operation control unit 8 while the internal organ composition impedance Zj is calculated in the CPU 13, using the measured voltages $V_9$ to $V_{12}$. Specifically, the above Equations 9 to 12 are used to calculate Equation 9+Equation 10−(Equation 11+Equation 12), so that the contact impedances are cancelled and the following equation holds.

$$2Zj\cdot I=V_9+V_{10}-(V_{11}+V_{12})$$

Therefore, $Zj=\{V_9+V_{10}-(V_{11}+V_{12})\}/2I$

From the above equation, the internal organ composition impedance Zj is obtained. The constant current value I is represented by I=v/Rs.

In the CPU 13, the amount of body fat in the internal organ is subsequently obtained from the internal organ composition impedance Zj and personal data which have been input beforehand, using the known calculation method. The amount of fat in the internal organ which has been thus obtained is displayed on the display unit 15 by way of the I/O circuit 12 to be transmitted to the patient.

According to the fourth embodiment, four measurement sites on the hands and feet of the patient are each provided with an electrode, so that an internal organ composition impedance, which excludes contact impedances and body distal site surrounding composition impedances in whole hands and feet (in contrast with this, the body composition impedance of the first embodiment excludes body distal site surrounding composition impedances around the feet) can be measured. With this arrangement, the amount of body fat in the internal organ can be stably, correctly measured. In consequence, the number of electrodes required for internal organ composition impedance measurement can be reduced, leading to a reduction in the number of wires and circuits and therefore a simplified system configuration. In addition, the same effect as that of the first embodiment can be obtained.

Although the internal organ composition impedance Zj is calculated based on four measurements (i.e., the measurement of the output voltages $V_9$ to $V_{12}$) made by switching the analog switches in the fourth embodiment, the calculation may be performed based on three measurements. Specifically, on assumption that the contact impedances $R_{41C}$ and $R_{41D}$ on the right and left hands are equal to each other; the composition impedances $Z_{41C}$ and $Z_{41D}$ on the right and left arms are equal to each other; the contact impedances $R_{41A}$, $R_{41B}$ on the right and left feet are equal to each other; and the composition impedances $Z_{41A}$ and $Z_{41B}$ on the right and left feet are equal to each other, Equation 11 can be converted into the following Equation 11'

$$2 \cdot (R_{41C} + Z_{41C}) = (V_{11} - Rs \cdot I)/I \qquad \text{(Equation 11')}$$

and Equation 12 can be converted into the following Equation 12'

$$2 \cdot (R_{41A} + Z_{41A}) = (V_{12} - Rs \cdot I)/I \qquad \text{(Equation 12')}.$$

Therefore, the internal organ composition impedance Zj is described by

Zj=Equation 9–(Equation 11'+Equation 12')/2, and can be measured based on three measurements (i.e., the measurements of the output voltages $V_9$, $V_{11}$, $V_{12}$) by switching the analog switches. In addition, it is also possible to obtain the internal organ composition impedance Zj by allowing a current to diagonally flow in the body of the patient with, for instance, only the analog switches 43f, 43b turned ON.

The fourth embodiment may be arranged such that like the first embodiment, the body fat measurement circuit 18 is disposed within the arithmetic operation circuit 8 so as to be switchable to make a weight measurement at the same time with a measurement of the amount of body fat in an internal organ. In this case, it is possible to measure the internal organ composition impedance Zj by employing the measurement sequence of the first embodiment and utilizing the wait time until a weight value becomes stable.

In each of the foregoing embodiments, body weight signals (weight signals) and impedance signals (output voltage signals $V_1$ to $V_4$) are digitized by the same A/D converter 11. The invention is not limited to this, but may be arranged differently. For example, there may be provided an A/D converter for the body composition impedance measurement circuit and an A/D converter for the weight measurement circuit, and the weight signals and the impedance signals are converted by their respective A/D converters.

In each of the foregoing embodiments, the value of body weight (weight value) and the amount of body fat (body fat percentage) are alternately displayed at specified time intervals on the same display unit 15. The invention is not limited to this but may be arranged such that the value of weight and the amount of body fat are displayed on different display units or may be arranged such that these values are selectively displayed on the same display unit by depressing a key switch.

Figure 8:
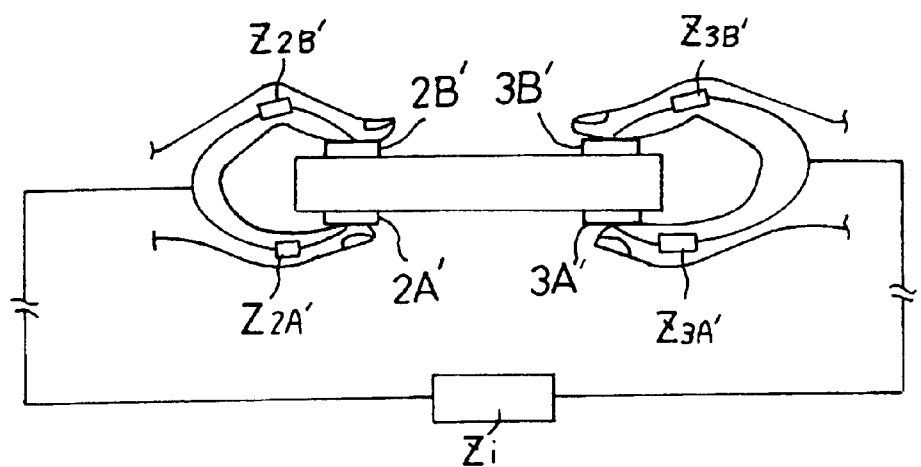
FIG. 8 is an explanatory diagram illustrating another form of the first to third embodiments.
Figure 9A:
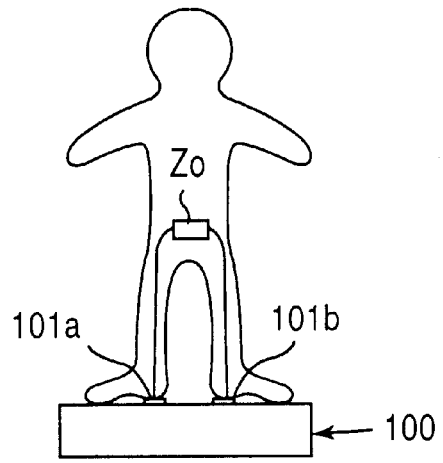
FIG. 9(a) is a principle diagram illustrating the principle of body composition impedance measurement in a prior art body fat measuring device.
Figure 9B:
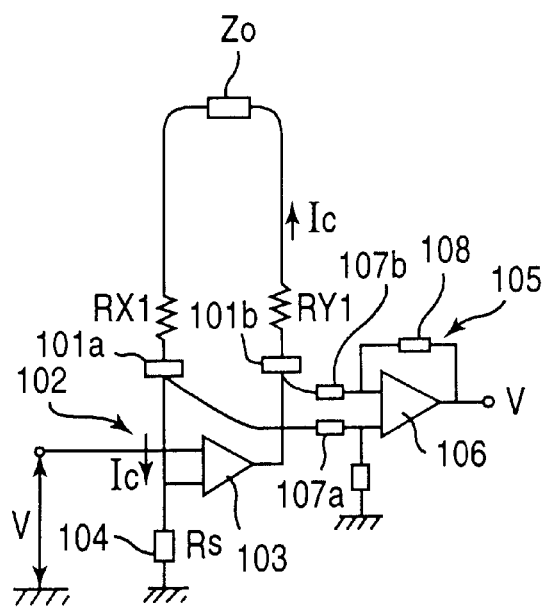
FIG. 9(b) is a circuit diagram illustrating the principle of the measurement.
Figure 10A:
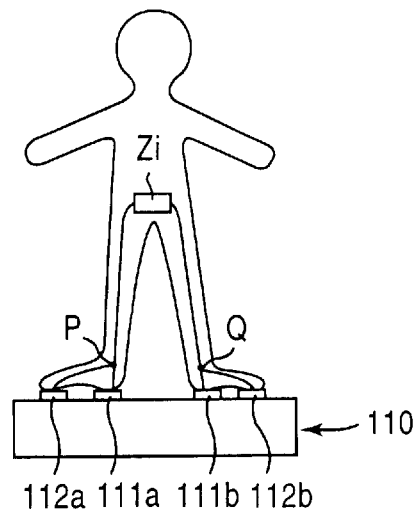
FIG. 10(a) is a principle diagram illustrating the principle of body composition impedance measurement in another prior art body fat measuring device.
Figure 10B:
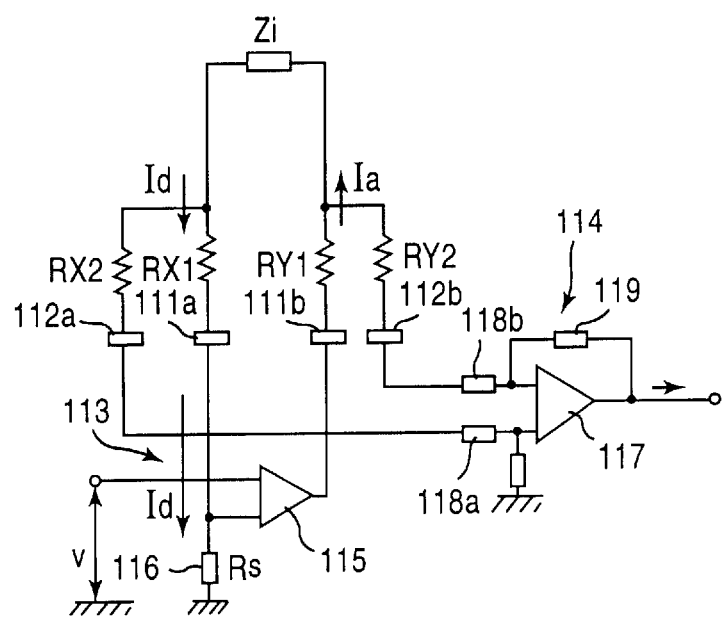
FIG. 10(b) is a circuit diagram illustrating the principle of the measurement.
Figure 11:
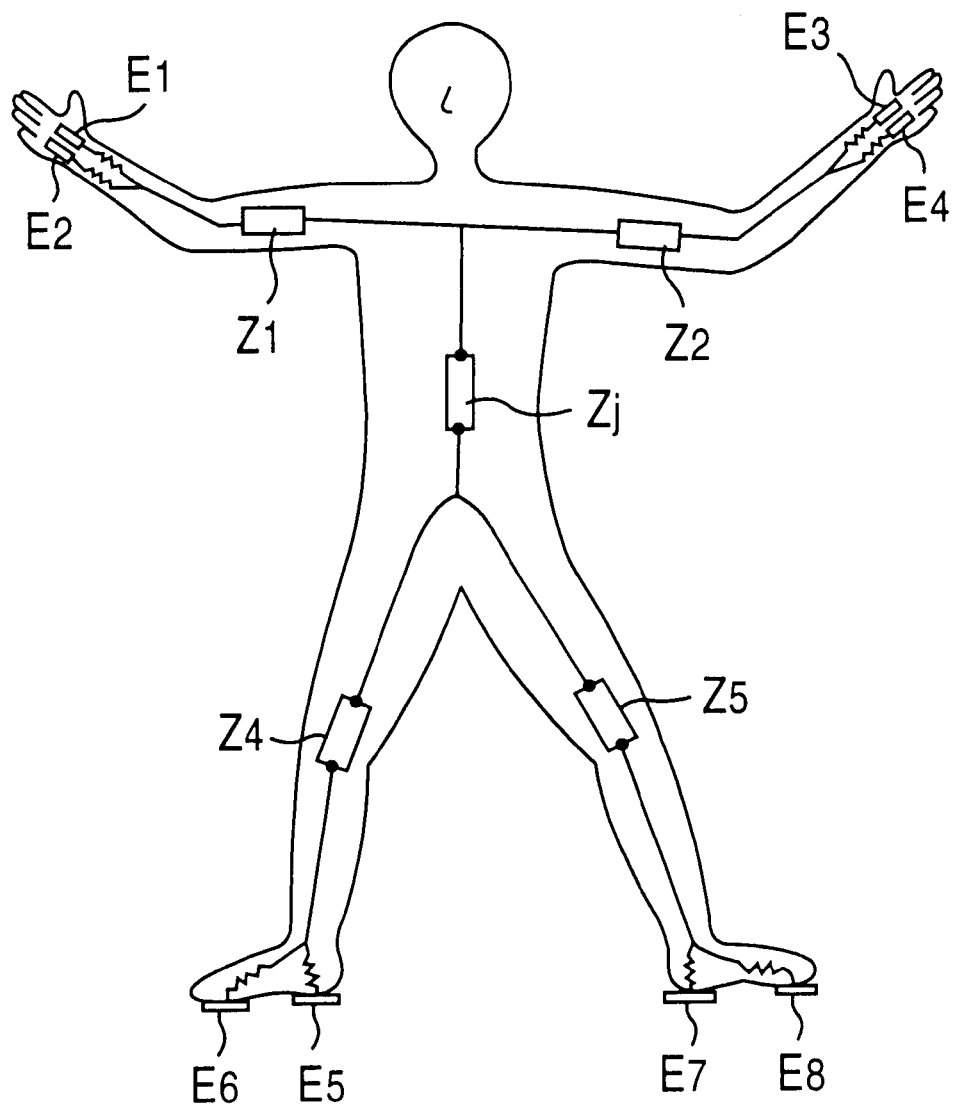
FIG. 11 is a principle diagram illustrating the principle of internal organ composition impedance measurement in another prior art body fat measuring device.

While the body composition impedance Zi is measured with the backs of the feet in contact with the electrodes in the first to third embodiments, the body composition impedance Zi can be similarly measured by putting the electrodes (2A', 2B', 3A', 3B') between the fingers of both hands as shown in FIG. 8. In this case, since the body distal site surrounding composition impedances are eliminated although the measurement route includes many articulates having great impedance values, the amount of body fat can be measured with high accuracy.

In cases where the measuring device includes the weight measurement circuit 18 in the first to third embodiments, the electrodes are preferably placed on the weight measuring surface. It is also possible to place some electrodes at positions which are touchable or graspable by hands or fingers while others being placed at the weight measuring surface. In cases where the measuring device does not have the weight measurement circuit 18 or where the weight measuring section is separated from the body fat measuring section, the electrodes may be placed at positions touchable or graspable by hands or fingers, or alternatively, some electrodes may be placed at positions touchable or graspable by hands or fingers while others being placed at the weight measuring surface.

What is claimed is:

1. A body fat measuring device for measuring the amount of body fat within a body, the device comprising:

(a) a single or a plurality of electrodes in contact with each of a plurality of sites on the dermal surface of the body;

(b) a power supply circuit for applying a constant current or voltage to the electrodes;

(c) impedance measuring means for switching the electrodes to be connected to the power supply circuit such that a contact impedance and a body distal site surrounding composition impedance are present between the electrodes or such that a contact impedance, a body distal site surrounding composition impedance and a body composition impedance are present between the electrodes, whereby the value of the composite of the contact impedance and the body distal site surrounding composition impedance and the value of the composite of the contact impedance, the body distal site surrounding composition impedance and the body composition impedance are respectively measured; and (d) calculating means for calculating the value of the body composition impedance based on the measured values obtained by the impedance measuring means.

2. A body fat measuring device according to claim 1, wherein the electrodes are provided such that a pair of electrodes are disposed so as to contact a first one of two dermal surface sites between which a body composition impedance to be measured is present and another pair of electrodes are disposed so as to contact a second one of the dermal surface sites;

wherein the electrodes in each pair are close to each other;

wherein the power supply circuit is connected to the pair of electrodes at the first site or at the second site by the impedance measuring means to measure the value of the composite of a contact impedance and a body distal site surrounding composition impedance, said impedances being present between the pair of electrodes to which the power supply circuit is connected; and wherein the power supply circuit is connected to one of the electrodes in the respective pairs at the first site and at the second site to measure the value of the composite of a contact impedance, a body distal site surrounding composition impedance and a body composition impedance, said impedances being present between the pair of electrodes to which the power supply circuit is connected; and wherein the calculating means calculates the value of the body composition impedance based on the measured values.

3. A body fat measuring device according to claim 1, wherein the electrodes are provided such that two electrodes are disposed so as to contact a first one of two dermal surface sites between which a body composition impedance to be measured is present and one electrode is disposed so as to contact a second one of the two sites;

wherein the two electrodes disposed at the first site are close to each other;

wherein the power supply circuit is connected to the two electrodes at the first site by the impedance measuring means to measure the value of the composite of a contact impedance and a body distal site surrounding composition impedance, said impedances being present between the pair of electrodes to which the power supply circuit is connected;

wherein the power supply circuit is connected to one of the electrodes at the first site and the electrode at the second site to measure the value of the composite of a contact impedance, a body distal site surrounding composition impedance, and a body composition impedance, said impedances being present between the pair of electrodes to which the power supply circuit is connected; and wherein the calculating means calculates the value of the body composition impedance based on the measured values.

4. A body fat measuring device according to claim 1, wherein the electrodes are provided such that one electrode is disposed so as to contact each of the dermal surface sites surrounding hands and feet respectively;

wherein the power supply circuit is connected by the impedance measuring means to the electrode in contact with one hand and to the electrode in contact with one foot to measure the value of the composite of a contact impedance, an arm composition impedance, a leg composition impedance and an internal organ impedance, said impedances being present between the pair of electrodes to which the power supply circuit is connected;

wherein the power supply circuit is connected to the electrodes in contact with the hands to measure the value of the composite of a contact impedance and an arm composition impedance, said impedances being present between the electrodes to which the power supply circuit is connected;

wherein the power supply circuit is connected to the electrodes in contact with the feet to measure the value of the composite of a contact impedance and a leg composition impedance, said impedances being present between the pair of electrodes to which the power supply circuit is connected; and wherein the calculating means calculates the value of the internal organ composition impedance, based on the measured values.

5. A body fat measuring device according to any one of claims 1 to 4, which further comprises weight measuring means.

6. A body fat measuring device according to claim 5, wherein the measurement of the impedances by the impedance measuring means is carried out while weight measurement being made by the weight measuring means, during a transient weight phenomenon state in which weight fluctuates.

7. A body fat measuring device according to claim 6, wherein when the value of weight measured by the weight measuring means significantly fluctuates, being in an unstable condition, the measurement of the impedances between the electrodes by the impedance measuring means is carried out while the weight measurement by the weight measuring means being made.

8. A body fat measuring device according to claim 6, wherein when the value of weight measured by the weight measuring means does not fluctuate so much, being in a stable condition, the measurement of the impedance between the electrodes by the impedance measuring means is interrupted.

9. A body fat measuring device according to claim 5, wherein when the value of weight measured by the weight measuring means significantly fluctuates, being in an unstable condition, the measurement of the impedances between the electrodes by the impedance measuring means is carried out while the weight measurement by the weight measuring means being made.

10. A body fat measuring device according to claim 5, wherein when the value of weight measured by the weight measuring means does not fluctuate so much, being in a stable condition, the measurement of the impedance between the electrodes by the impedance measuring means is interrupted.

11. A body fat measuring device according to claim 10, wherein when the value of weight measured by the weight measuring means does not fluctuate so much, being in a stable condition, the measurement of the impedances between the electrodes by the impedance measuring means is interrupted while only the weight measurement being made.

* * * * *